United States Patent [19]
Hugh

[11] Patent Number: 5,645,554
[45] Date of Patent: Jul. 8, 1997

[54] TREPHINATOR FOR TREATING SUBUNGUAL HEMATOMAS

[76] Inventor: Donald C. Hugh, 26137 Marina Dr., Rolling Hills Estates, Calif. 90274

[21] Appl. No.: 645,651

[22] Filed: May 14, 1996

[51] Int. Cl.[6] ................................................ A61B 17/14
[52] U.S. Cl. ........................................ 606/180; 606/172
[58] Field of Search ................................ 606/180, 170, 606/159, 171, 172; 408/202, 226; 81/451

[56] References Cited

U.S. PATENT DOCUMENTS

| | | | |
|---|---|---|---|
| 696,902 | 4/1902 | Gray | 606/180 |
| 854,956 | 5/1907 | Martin . | |
| 3,628,522 | 12/1971 | Kato | 128/2 B |
| 3,688,386 | 9/1972 | Pereira | 29/558 |
| 3,989,033 | 11/1976 | Halpern et al. | 128/2 B |
| 4,267,841 | 5/1981 | Fraser | 128/305 |
| 4,526,171 | 7/1985 | Schachar | 128/305 |
| 4,821,716 | 4/1989 | Ghajar et al. | 606/172 |
| 4,995,877 | 2/1991 | Ams et al. | 606/180 |
| 5,366,468 | 11/1994 | Fucci et al. | 606/180 |
| 5,423,824 | 6/1995 | Akerfeldt et al. | 606/180 |

*Primary Examiner*—Guy V. Tucker
*Assistant Examiner*—Kevin Troung
*Attorney, Agent, or Firm*—Gene Scott-Patent Law and Venture Group

[57] ABSTRACT

A nail boring device uses a common drill bit to penetrate a traumatized nail having collected fluids trapped below it. A novel depth of penetration control device is used with the bit to assure that a bored hole is only as deep as necessary and that the process may proceed in small steps acceptable to the patient. A method of approach necessary to the successful use of the device is described.

5 Claims, 2 Drawing Sheets

TREPHINATOR FOR TREATING SUBUNGUAL HEMATOMAS

BACKGROUND OF THE INVENTION

1. Field of the Invention

This invention relates generally to boring devices, and more particularly to a boring device and depth of penetration control for relieving the discomfort of subungual hematomas.

2. Description of Related Art

Invention and use of devices in the field of the invention is known to the public, as they are used for the intended purposes as defined herein. The following art defines the state of this field at this time:

The device shown in FIG. 2 is a common electrically heated tool used by the medical profession to open and drain a subungual hematoma. The use of this device usually causes immediate pain and anxiety.

Ams et al., U.S. Pat. No. 4,995,877, teaches a rotationally driven surgical instrument incorporating a hand-held element having a mount rotatably installed for reception of interchangeable cutting and milling inserts, a driving motor for driving the mount receiving the tool inserts, a control unit for controlling the driving motor with means of setting the rotational speed and for pre-selecting the rotational speed range and direction of rotation, and a digital indicator for displaying the rotational speed set up in each case.

Fucci et al., U.S. Pat. No. 5,366,468, shows a surgical router used for cutting anatomical tissue. The router includes an outer tubular member and an inner tubular member. The outer part holds the inner part and a pair or blades equally spaced on the longitudinal axis of the inner member and a pair of flutes disposed between the blades. The flute bottoms angularly intersect the inner member to form aspiration ports within integral with the flutes. The blades have leading walls, trailing walls, and clearance walls with a width between the trailing walls that tapers in a distal direction. The leading walls correspond to the flute sides and curve around the inner member axis in the direction of rotation of the inner member in the outer member. End and side cutting edges are disposed along the leading walls with the end cutting edges being curved about the inner member axis in accordance with the curvature of the leading walls, and the side cutting edges extend longitudinally, helically along the inner member. Center cutting surfaces join the clearance walls and leading walls at notches in the inner member distal end, and the meeting of the center cutting services with the clearance walls define center cutting edges angled from the end cutting edges in the direction of rotation of the inner member in the outer member.

Halpern et al., U.S. Pat. No. 3,989,033, shows a surgical instrument for extracting specimens from an organ. The instrument comprises configured cutting elements. The elements are arranged so that they penetrate the organ by cylindrical incision, and then perform a finishing cut which separates the specimen. The first embodiment of the instrument shows the cutting elements, a punch and rotating guillotine or knife. The second embodiment shows two faced clamps, which replace the guillotine. The clamps are in the form of a churn, trough or convex, having a sharp point and sharp longitudinal edges.

Kato U.S. Pat. No. 3,628,522, shows a surgical instrument that has a pair of pivotally mounted blades for removing a conical section. The blades are coupled by linkage so their movement is controlled as the handle acts as a sleeve to permit angular rotation with which the blades co-act. The linkage includes a pair of pivotally mounted support arms, which extend outwardly. The arms, when retracted, partially extend within a slot in their supporting device and overlap each other.

Peteira U.S. Pat. No. 3,688,386, shows a method of fenestrating contact lenses by use of a series of very small tools, specifically a small hand drill, a tapered reamer, and a tool having a 90 degree point to bevel the edges of the hole, and a polishing and smoothing device combined with the beveling tool so to give a polish to the edges of the hole. The method is carded out by first drilling the hole, reaming the hole to a predetermined size, bevelling, and then polishing the edges of the hole.

Fraser U.S. Pat. No. 4,267,841, shows a nail matrix trephine that uses a clamping head for clamping the trephine to a nail plate and a guide head for guiding a trephine cutter. The clamping head and guide are interconnected by an adjustment device so that when the head is clamped to the nail plate, the guide head is adjusted so that the trephine cutter is guided to remove preselected nail matrix cells.

Martin U.S. Pat. No. 854,956, shows a drilling and puncturing device consisting of two parts, the shaft having the enlarged part, to bear against the abutment, and the detachable puncturing part, which is connected to the spindle by a screw-joint. This screw-joint permits using different forms of drilling or puncturing tools, to be used as needed. The drill point has a reduced part, which is embraced by the friction and abutment blocks. The tension of the springs cause these blocks to bear on the reduced part of the drill point with considerable pressure. The enlarged part of the shaft turns with the drill spindle in the casing and forms one bearing, and the other bearing for the drill spindle is the combined abutment and carrier. A sleeve with shoulder embraces the drill spindle, and a knurled ring, which is screw-threaded once at the end of the casing, against the part so that the drill spindle and drill point cannot move longitudinally.

Schachar, U.S. Pat. No. 4,526,171, discloses an invention which relates to correcting vision defects, and more particularly to changing the curvature of the human cornea by the formation of incisions on the surface of the cornea.

The prior art presented here discloses several approaches to controlled penetrations on varying scales. However, these references do not disclose a device for controlling the depth of miniature bores in small steps in such manner that any person can easily accomplish the task without training. The prior art devices also do not teach a very inexpensive approach which is necessary to the wide spread use of the present invention. The present invention fulfills these needs and provides further related advantages as described in the following summary.

SUMMARY OF THE INVENTION

Trauma to a hand or foot, after, for instance, having been struck a severe blow, usually causes blood to collect and pool under a finger or toe nail. The medical term for this general condition is subungual hematoma. The result is throbbing pain caused, not only by damage to nerve endings, but to a great extent, by the trapping of blood in an ever smaller space as swelling occurs. The clotting and drying of the blood quickly changes color from red, to purple, to black. This discoloration is frequently referred to as "black nail" and may last for months. In most cases, if nothing is done to relieve the damage to the nail caused by the blood collection, the nail will eventually fall off. By directing the pooling blood out of the restricted space under the nail, several beneficial results occur. First, the pressure under the nail is relieved so that the swelling and throbbing pain is avoided. Second, the discoloration of the nail is lessened or completely avoided. Finally, premature loss of the nail is avoided.

In order to relieve the blood from under the nail it is necessary to bore a small hole in the nail. However, boring such a hole is considered painful and usually avoided. When finger pain is so great as to force such a procedure, medical help is usually obtained. The present invention teaches a simple and painless approach to boring such a hole which is quickly accomplished without difficulty by the patient him/herself. The invention includes a small hole boring instrument having a fluted drill portion, a handle for manipulation of the drill, and a depth of penetration portion for controlling how deep the drill portion may proceed. Thus it is an object of the present invention to provide a nail boring device capable of boring a small hole in a nail to relieve pressure thereunder. It is an important object of the present invention to provide such a nail boring device, further having an effective depth of penetration control means that is easily and minutely adjusted so that the user can proceed with ever deeper penetrations in a step by step process that is psychologically acceptable to a person in great pain. It is an important object of the present invention to, provide a step by step procedure for use of the present invention device in such manner as to be, at once, fully effective in relieving pressure under a damaged nail, to accomplish such result without further pain to the patient, and to overcome the fears of the patient. It is a further important object of the present invention to provide such means of relieving pressure and pain in finger and toe trauma that is inexpensive to manufacture and provide in the marketplace. The above objectives are achieved by the present invention in a manner that is new to the art, extremely cost effective and may be applied by any person having simple manual manipulation skills.

The primary inventive step in the present invention is the recognition of, and reduction to practice, of the combination of a tube of relatively soft material and a common spiral fluted drill bit in such a manner that the combination is able to be used in a step by step penetration of a finger or toe nail to overcome the physical and emotional problems presently associate with subungual hematoma.

Other features and advantages of the present invention will become apparent from the following more detailed description, taken in conjunction with the accompanying drawings, which illustrate, by way of example, the principles of the invention.

BRIEF DESCRIPTION OF THE DRAWING

The accompanying drawings illustrate the present invention, a device for boring one or more holes in a finger or toe nail in order to relieve pressure of a trauma. In such drawings.

DETAILED DESCRIPTION OF THE PREFERRED EMBODIMENT

Figure 3:
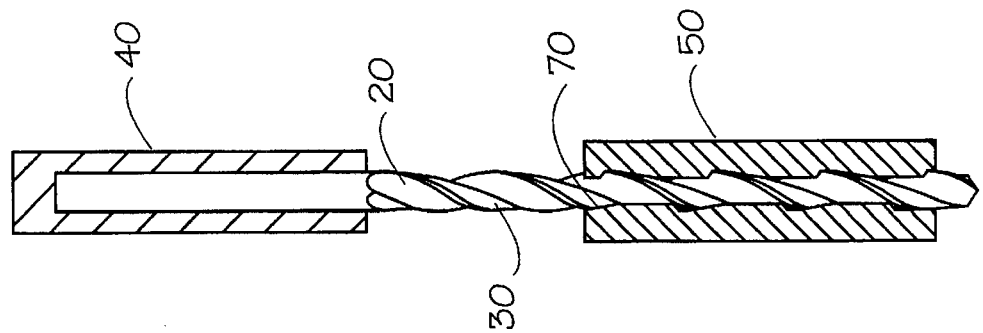
FIG. 3 is an elevational side view of the present invention showing a hole boring portion, a handle portion and a penetration controlling portion.
Figure 4:
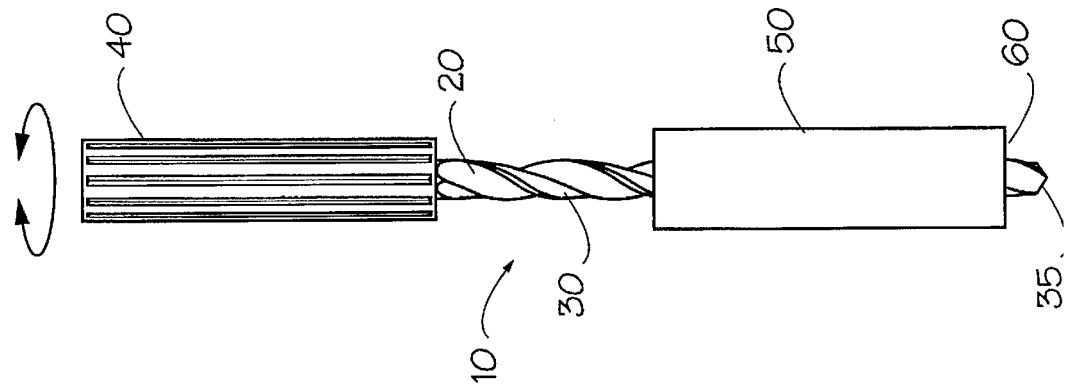
FIG. 4 is a cross-sectional view thereof taken through a vertical central cutting plane in FIG. 3.
Figure 2:
FIG. 2 is a perspective view of a prior art electrical burning device used to puncture and open a draining aperture in a finger or toe nail.
Figure 1:
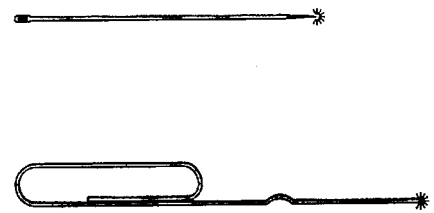
FIG. 1 shows an elevational view of two prior art devices used by medical professionals to puncture a finger nail for draining fluids. These devices are generally heated.
Figure 6:
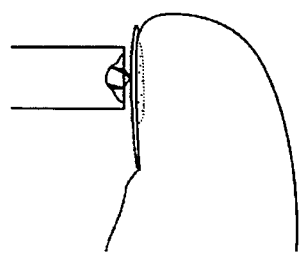
FIGS. 6–8 are close-up views of a portion of that shown in FIG. 5 illustrating further, the manner in which the present invention is applied, i.e., the start of an initial hole, further penetration, and final penetration, respectively.
Figure 7:
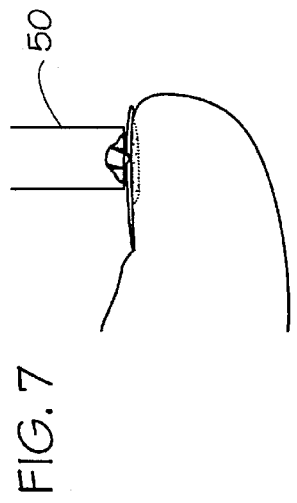
Figure 8:
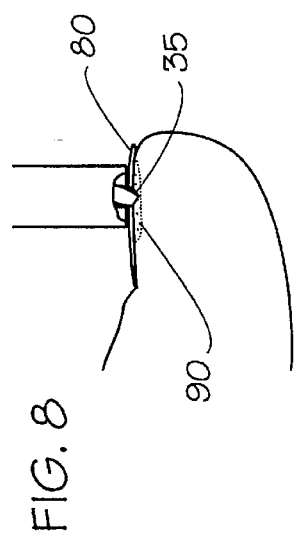
Figure 5:
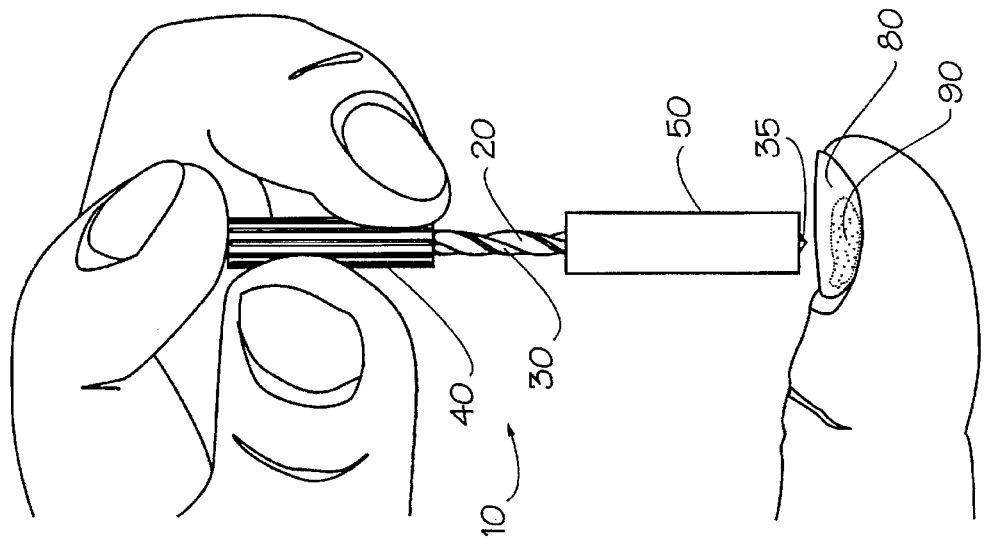
FIG. 5 is a view similar to that shown in FIG. 3, illustrating the manner in which the invention is held and applied.

The above described drawing figures illustrate a device for boring a finger or toe nail in order to relieve fluid pressure. First, the device provides an elongate means for boring a hole 10, the hole boring means provides a side 20 having at least one cutting flute 30 impressed therein and further providing a cutting edge 35 at the end of the hole boring means 10. Preferably, the hole boring means 10 is a miniature drill bit of the type shown in FIGS. 3 and 4, which is preferably between 1.0 and 1.5 mm in diameter, rather then the prior art type racleurs or rasp shown in FIGS. 1 and 2. It has been discovered that the fluted drill bit type shown in FIGS. 3–8 is particularly suited for the intended objects in that it is able to drill a full sized hole and not a narrow one, which must later be widened, it is able to proceed with a gradual penetration, and it has the ability to communicate with the penetration controlling means of the invention for an effective and inexpensive result. A means for holding 40 the hole boring means 10 so that the device may be manually rotated is provided. Such a holding means is preferably an elongate handle as best seen in FIG. 3. Finally, a means for controlling drilling depth 50 of the hole boring means 10, is provided. The depth control means 50 is preferably a tube having an end shoulder 60 and an internal side wall 70, as best seen in FIG. 4. The at least one cutting flute 30 is preferably spiral shaped. The cutting flute 30 is self tapped into the internal side wall 70 of the tube 50 such that the tube is movable along the side wall 70 only by rotating the tube 50 around the side wall for positioning of the end shoulder 60 relative to the cutting edge 35. The end shoulder 60 therefore prevents advancement of the cutting edge 35 into a surface 80 to be bored such as that of a finger or toe nail thereby determining the depth of penetration. It has been discovered that it is an easy matter to "thread" the tube 50 onto the boring means 10 if the tube 50 is made of a material that is soft enough to be cut by the flute(s) 30, thereby allowing self tapping of the tube by the flutes. The tube 50 is then constrained to move in rotation on the boring means by the flute so that the advancement and positioning of the tube 50 is highly controlled.

The method of use of the present invention for boring a nail comprises certain preferred steps including, positioning the end shoulder 60 of the depth controlling means 50 near the cutting edge 35 of the hole boring means 10, positioning the cutting edge 35 over a subungual hematoma 90 and in contact with a surface 80 of a nail to be bored, rotating the cutting edge 35, ¼ rotation clockwise and then ¼ rotation (approximately) counterclockwise in turn, alternately, driving the cutting edge 35 into the nail, until the depth end shoulder 60 contacts the surface 80 of the nail, adjusting the end shoulder 60 away from the cutting edge 35, and then repeating these steps in turn repetitively for small incremental advancements of the cutting edge through the nail until a fluid flows from the penetration. Adjustment of the end shoulder 60 is accomplished by rotating the tube 50 on the side wall 20 of the boring means 10. The tube 50 is constrained to follow the spiral path of the flute 30 so that is linear advancement along the side wall 20 is highly controlled. After draining the fluid from the nail, the nail may be soaked in warm water and massaged to completely flush out all of the blood and other fluids. If the hematoma 90 is large, then several holes may be bored to effectively drain all trapped fluids. The nail may be further soaked in a solution of hydrogen peroxide or hypochlorite in order to bleach away any residue of the black color under the nail. Because the penetrations are an avenue for germs to enter and grow, it is advisable to treat the resulting bored holes as one would treat any open wound.

While the invention has been described with reference to at least one preferred embodiment, it is to be clearly understood by those skilled in the art that the invention is not limited thereto. Rather, the scope of the invention is to be interpreted only in conjunction with the appended claims.

What is claimed is:

1. A nail boring device comprising:

an elongate means for boring a hole, the hole boring means providing a side wall having at least one cutting flute impressed therein and further providing a cutting edge;

a means for holding the hole boring means so that the device may be manually rotated;

a means for controlling drilling depth of the hole boring means;

the depth controlling means being a tube having an annular end shoulder extending around the boring means and an internal circular side wall, the side wall being engaged with the at least one flute enabling the tube to move longitudinally along the hole boring means as the tube rotates on the hole boring means.

2. The device of claim 1 wherein the at least one cutting flute is self tapped into the internal side wall of the tube such that the tube is movable along the side wall only by rotating the tube thereon for positioning of the end shoulder relative to the cutting edge, the end shoulder preventing advancement of the cutting edge into a surface to be bored.

3. The device of claim 1 wherein the side wall of the tube is in contact with the at least one flute, the side wall being soft enough to engage the at least one flute such that the tube is movable along the side wall only by rotating the tube thereon for positioning of the end shoulder relative to the cutting edge, the end shoulder preventing advancement of the curing edge into a surface to be bored.

4. A method of boring a nail comprising the steps of:

a) providing an elongate means for boring a hole, the hole boring means providing a side wall having at least one cutting flute impressed therein and further providing a cutting edge, and a means for holding the hole boring means so that the device may be manually rotated, and a means for controlling drilling depth of the hole boring means, the depth controlling means being tubular and having an end shoulder and an internal side wall being self tapped engaged by the at least one cutting flute for relative axial movement by rotation thereon;

b) positioning the end shoulder of the depth controlling means near the cutting edge of the hole boring means;

c) positioning the cutting edge over a subungual hematoma and in contact with a surface of a nail to be bored;

d) rotating the cutting edge ¼ rotation clockwise and then ¼ rotation counterclockwise in turn, alternately, driving the cutting edge into the nail, until the depth controlling means contacts the surface of the nail;

e) adjusting the end shoulder away from the cutting edge;

f) repeating steps (d) and (e) in turn repetitively for small incremental advancements of the cutting edge through the nail until a fluid flows from the penetration.

5. A method of boring a nail comprising the steps of:

a) providing an elongate means for boring a hole, the hole boring means providing a cutting edge, and a means for holding the hole boring means so that the device may be manually rotated, and a means for controlling drilling depth of the hole boring means, the depth controlling means being engaged by the cutting edge;

b) positioning an end shoulder of the depth controlling means near the cutting edge;

c) positioning the cutting edge over a subungual hematoma and in contact with a surface of a nail to be bored;

d) rotating the cutting edge alternately clockwise and counterclockwise in turn, driving the cutting edge into the nail, until the depth controlling means contacts the surface of the nail;

e) adjusting the end shoulder to further expose the cutting edge;

f) repeating steps (d) and (e) in turn repetitively for small incremental advancements of the curing edge through the nail until a fluid flows from a penetration of the hole boring means through the nail.

* * * * *